United States Patent [19]
Beriger et al.

[11] 3,992,533
[45] Nov. 16, 1976

[54] O-ETHYL-S-n-PROPYL-O-(2-CHLORO-4-BROMOPHENYL)-THIOPHOSPHATE

[75] Inventors: Ernest Beriger; Jozef Drabek, both of Allschwil, Switzerland

[73] Assignee: Ciba-Geigy Corporation, Ardsley, N.Y.

[22] Filed: Mar. 14, 1975

[21] Appl. No.: 558,589

Related U.S. Application Data

[63] Continuation-in-part of Ser. No. 429,425, Dec. 28, 1973, abandoned, which is a continuation of Ser. No. 295,407, Oct. 5, 1972, abandoned.

[30] Foreign Application Priority Data

Oct. 12, 1971 Switzerland.................... 14855/71

[52] U.S. Cl.................................. 424/225; 260/964
[51] Int. Cl.[2]...................... A01N 9/36; C07F 9/165
[58] Field of Search..................... 260/964; 424/225

[56] References Cited
UNITED STATES PATENTS

| | | | |
|---|---|---|---|
| 3,530,206 | 9/1970 | Beriger | 260/964 |
| 3,839,511 | 10/1974 | Kishino et al. | 260/964 |

*Primary Examiner*—Anton H. Sutto
*Attorney, Agent, or Firm*—Frederick H. Rabin

[57] ABSTRACT

The thiophosphoric acid phenylester of the formula

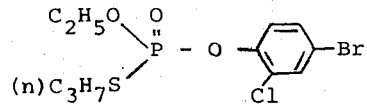

its manufacture and use in pest control is disclosed.

4 Claims, No Drawings

O-ETHYL-S-n-PROPYL-O-(2-CHLORO-4-BROMO-PHENYL)-THIOPHOSPHATE

CROSS REFERENCES

This is a continuation in part of application Ser. No. 429,425 filed Dec. 28, 1973 which itself is a continuation of application Ser. No. 295,407 filed Oct. 5, 1972, both now abandoned.

This invention relates to the thiophosphoric acid phenylester of the formula

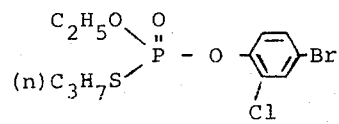 (I) 

Another subject is the manufacture of the compound of the formula I and its use as active ingredient in pesticidal especially insecticidal preparations.

The compound of formula I is most generally disclosed in French Pats. Nos. 1,295,613 and 1,567,444. A disclosure of even more closely related compounds — such as e.g. the O-ethyl-S-n-propyl-O-(2,4-dichlorophenyl)- and O-ethyl-S-n-propyl-O-(2,4-dibromophenyl)-thiophosphoric acid ester — is to be found in the U.S. Pat. No. 3,839,511. Accordingly the instant compound is a selection out of the latter U.S. Patent and shows surprisingly superior activities on at least the same toxicity level as the closest known compounds, especially with respect to its initial effect towards cotton pests.

The new thiophosphoric acid phenylester may be prepared according to known processes such as:

1a) 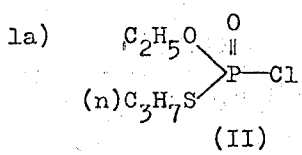 + 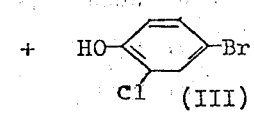 $\xrightarrow{\text{acid binding agent}}$ I

1b) 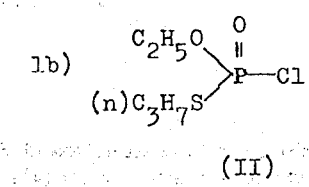 + 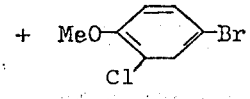 $\longrightarrow$ I

2) 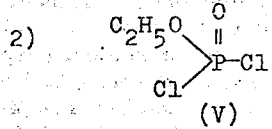 + 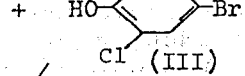

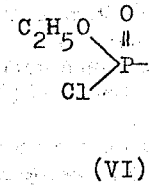 +  $\xrightarrow{\text{acid binding agent}}$ I

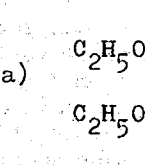 +  $\longrightarrow$ I

3a)

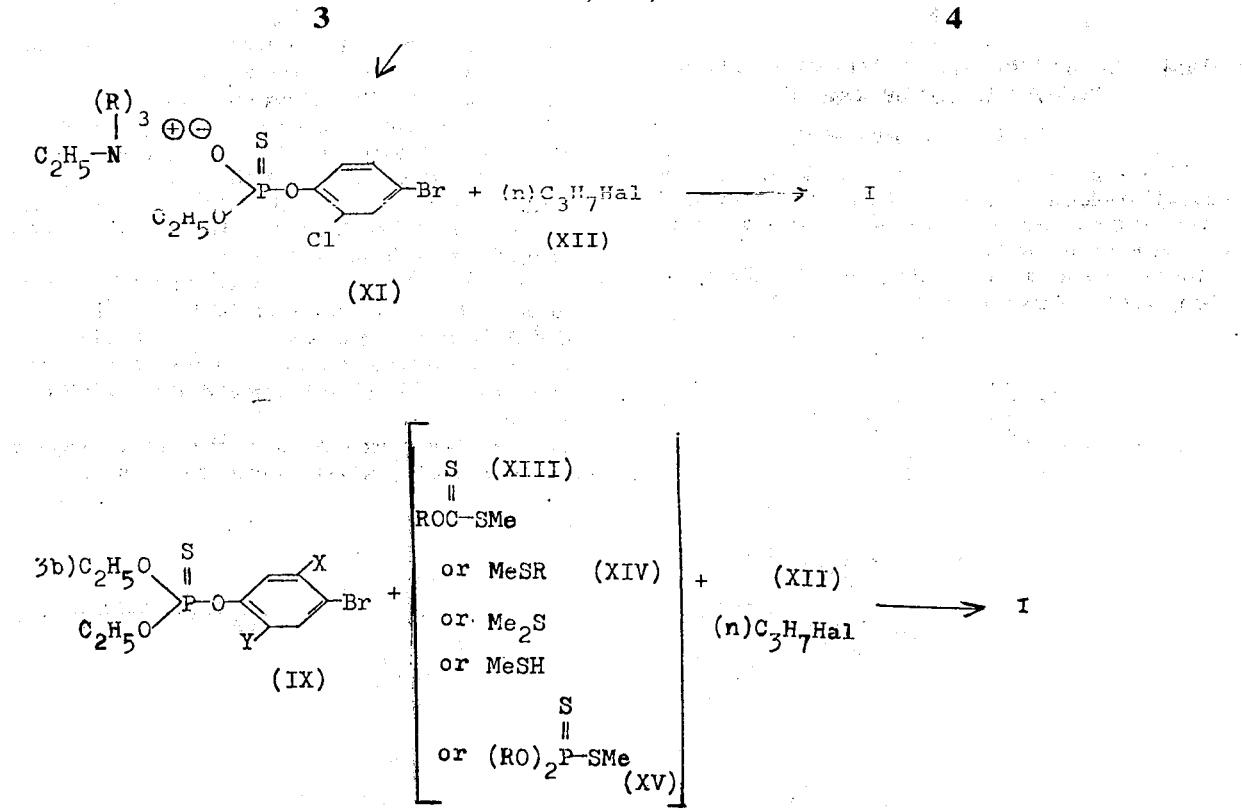

In the above formulae Me represents an alkali metal, particularly sodium or potassium, ammonium or alkylammonium, R stands for a $C_1$—$C_4$ alkyl radical, especially methyl or ethyl and Hal is a halogen atom such as iodine especially however chlorine or bromine.

As acid binding agents there may be used tertiary amines, e.g. trialkylamines, pyridine or dialkylanilines; also suitable are inorganic bases such as hydrides, hydroxides, carbonates and bicarbonates of alkali and alkaline earth metals. Depending on the reaction conditions it may be desirable in order to enhance the yield or reduce the duration of the reaction to use a catalyst such as e.g. copper or copper chloride. The processes 1a to 3b are carried out at a reaction temperature between 0° and 130° C, at normal pressure and in solvents or diluents inert to the reactants. Suitable as inert solvents or diluents are for example ethers and ethereal compounds such as diethyl ether, dipropyl ether, dioxane, tetrahydrofurane; amides such as N,N-dialkylated carboxylic acid amides; aliphatic and aromatic hydrocarbons, which may be halogenated particularly benzene, toluene, xylene, chloroform, chlorobenzene; nitriles such as acetonitrile; DMSO. For processes 3a and 3b alcohols such as ethanol, n-propanol or isopropanol are also suitable.

The starting material of formula II can be made by methods analogous to those described for example in J. Org. Chem. 30, 3217 (1965).

The compound of formula I has a broad insecticidal and acaricidal spectrum, the activity against plantpathogenic pests being emphasized. The compound acts above all as contact and stomac poison and thus can be used for the control of all development stages such as eggs, larvae, nymphs, pupae and adults of sucking, chewing and boring pests and mites. Noxious individuals of this kind are to be found in the field of grape, soya, maize, tobacco, forest and stored products pests. Most valuable results however are achieved against pests noxious to cotton and vegetables. In this connection the following families of insects and acarina must be considered: Chrysomelidae, Curculionidae, Dermestidae, Nitidulidae, Tenebrionidae; Anthomyiidae; Aleyrodidae, Aphididae, Psyllidae; Tenthredinidae; Gelechiidae, Geometridae, Hyponomeutidae, Lymantriidae, Lyonetiidae, Noctuidae, Olethreutidae, Phaloniidae, Pieridae, Plutellidae, Pyralidae, Tortricidae; Thripidae; Tetranychidae. The insecticidal and/or acaricidal effects can be substantially broadened and matched to given circumstances by the addition of other insecticides or acaricides. Such additional active ingredients may be selected from the group of organophosphorus compounds, nitrophenols and derivatives thereof, ureas, carbamates, chlorinated hydrocarbons, pyrethrinlike compounds and amidines especially formamidines a most valuable representative of which is 1,1-dimethyl-2-(2'-methyl-4'-chlorophenyl)-formamidine.

The compound of formula I may be used as active substance alone or together with suitable carriers and/or additives. Suitable carriers and additives may be solid or liquid and correspond to the substances conventionally used in formulation technique such, for example, as solvents, dispersants, wetting agents, adhesives, thickeners, binders and/or fertilisers.

For application the instant compound may be processed to conventionally formulated preparations as they are commonly used in application technology. They may be used as concentrates or dilutions according to the circumstances. Examples of such preparations are

| | |
|---|---|
| in solid form: | dusts, scattering agents or granules; |
| in liquid form: | a) concentrates of active ingredient dispersible in water: wettable powders, pastes or emulsifiable concentrates; |
| | b) solutions |

The above pesticidal preparations may be manufactured in known manner by intimately mixing and/or grinding the active ingredient with the suitable carriers, optionally with the addition of dispersants or solvents which are inert towards the active substance. To manufacture dusts and scattering agents, the active substance is mixed according to known methods with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminum silicates (feldspar and mica), calcium and magnesium suphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc.

These substances can either be used alone or in admixture with one another. Also granular formulations can be easily manufactured according to known methods. To these mixtures may also be added stabilizers for the active ingredient and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Suitable additives are for example olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulfonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilize the active substance, surface-active substance and anti-foam agents (e.g. silicone oils) and, optionally solvents. Suitable additives are well known in the formulation technique and the manufacture of the concentrates is achieved by known methods.

For the preparation of solutions the active substance of formula I is dissolved in a suitable organic solvent, mixtures of solvents or in water. Such solvents are well known in the formulation technique. The content of active substance in the above described preparations is between 0.1% to 95% and most preferably between 2 and 50%. In this connection it should be mentioned that if the application is carried out from an aircraft or with some other suitable means, it is possible to use concentrations of up to 99.5% or even pure active substance. The application rate of active ingredient on the other hand is as a rule about 0.1 to 2.0 kg per hectar. The active substance of formula I can, for example, be formulated as follows:

Dusts

The following substances are used to manufacture (a) a 5% and (b) a 2% dust:

| | | |
|---|---|---|
| a) | 5 | parts of active ingredient |
| | 95 | parts of talcum |
| b) | 2 | parts of active ingredient |
| | 1 | part of highly disperse silica |
| | 97 | parts of talcum. |

The active ingredient is mixed with the carriers and ground.

Granules

The following substances are used to produce 5% granules:
5 parts of active ingredient
0.25 parts of epichlorohydrin
0.25 parts of cetyl polyglycol ether
3.50 parts of polyethylene glycol
91 parts of kaolin (particle size 0.3–0.8 mm).

The active ingredient is mixed with epichlorohydrin and dissolved in 6 parts of acetone; the polyethylene glycol and cetyl polyglycol ether are then added. The thus obtained solution is sprayed on to kaolin, and the acetone subsequently evaporated in vacuo.

Wettable powder

The following constituents are used for the preparation of (a) a 40%, (b) and (c) a 25% and (d) a 10% wettable powder:

| | | |
|---|---|---|
| a) | 40 | parts of active ingredient |
| | 5 | parts of sodium lignin sulphonate |
| | 1 | part of sodium dibutyl-naphthalene sulphonate |
| | 54 | parts of silica acid. |
| b) | 25 | parts of active ingredient |
| | 4.5 | parts of calcium lignin sulphonate |
| | 1.9 | parts of Champagne chalk/hydroxyethyl cellulose mixture (1:1) |
| | 1.5 | parts of sodium dibutyl naphthalene sulphate |
| | 19.5 | parts of silica acid |
| | 19.5 | parts of Champagne chalk |
| | 28.1 | parts of kaolin. |
| c) | 25 | parts of active ingredient |
| | 2.5 | parts of isooctylphenoxy-polyoxyethylene-ethanol |
| | 1.7 | parts of Champagne chalk/hydroxyethyl cellulose mixture (1:1) |
| | 8.3 | parts of sodium aluminum silicate |
| | 16.5 | parts of kieselgur |
| | 46 | parts of kaolin |
| d) | 10 | parts of active ingredient |
| | 3 | parts of a mixture of the sodium salts of saturated fatty alcohol sulfates |
| | 5 | parts of naphthalenesulphonic acid/formaldehyde condensate |
| | 82 | parts of kaolin. |

The active ingredient is intimately mixed, in suitable mixers, with the additives, the mixture being then ground in an appropriate mill and roller. Wettable powders are obtained which can be diluted with water to give suspensions of any desired concentration.

Emulsifiable concentrates:

The following substances are used to produce (a) a 10% (b) a 25% and (c) a 50% emulsifiable concentrate:

| a) | 10 | parts of active ingredient |
| --- | --- | --- |
| | 3.4 | parts of epoxidised vegetable oil |
| | 3.4 | parts of a combination emulsifier consisting of fatty alcohol polyglycol ether and alkylarylsulphonate calcium salt |
| | 40 | parts of dimethylformamide |
| | 43.2 | parts of xylene. |
| b) | 25 | parts of active ingredient |
| | 2.5 | parts of epoxidised vegetable oil |
| | 10 | parts of an alkylarylsulphonate/fatty alcohol-polyglycol ether mixture |
| | 5 | parts of dimethylformamide |
| | 57.5 | parts of xylene. |
| c) | 50 | parts of active ingredient |
| | 4.2 | parts of tributylphenol polyglycolic ether |
| | 5.8 | parts of calcium dodecylbenzenesulfonate |
| | 20 | parts of cyclohexanone |
| | 20 | parts of xylene |

From these concentrates it is possible to produce, by dilution with water, emulsions of any desired concentration.

Sprays

The following substances are used to manufacture (a) a 5% and (b) a 95% spray:

| a) | 5 | parts of active ingredient |
| --- | --- | --- |
| | 1 | part of epichlorohydrin |
| | 94 | parts of petrol (boiling range 160–190° C) |
| b) | 95 | parts of active ingredient |
| | 5 | parts of epichlorohydrin |

The following examples illustrate the manufacture and testing of the compound according to the present invention.

EXAMPLE 1 a. 31.1 g (0.15 mole) 2-chloro-4-bromophenol were dissolved in 150 ml benzene and 15.1 g triethylamine were then added. At 10–15° C, 32.0 g of 0-ethyl-S-n-propyl-chlorothiophosphate were added dropwise with continuous stirring. Stirring was then continued for 12 hours at room temperature. The mixture was washed with water, 3% $Na_2CO_3$ solution and water and dried over anhydrous sodium sulphate. The benzene was distilled off and the residue purified by distillation (at 130° C/0.01 torr). Yield: 49 g; refractive index $n_D^{20}$ 1.5466.

b. 71.8 g 0,0-diethyl-0(2-chloro-4-bromophenyl)-phosphorothioate were dissolved in an ethanolic solution of KSH (consisting of 9.5 g $H_2S$; 13.5 g KOH, and 120 ml ethanol) and boiled for 10 hours under reflux. The solvent was then distilled off and the residue dissolved in 1000 ml water whereupon the waterinsoluble portion was extracted with toluene. The aqueous layer was separated and mixed with 30 g n-propyl-bromide in 8 g methyl-ethyl-ketone. This mixture was kept for 6 hours at 70° to 77° C, then cooled and the oily reaction product separated and dried. Yield: 71 g; refractive index: $n_D^{20}$ 1.5466.

EXAMPLE 2

Potted cotton and tobacco plants respectively were sprayed with 125 ppm of active ingredient in the form of an aqueous emulsion. After the coating had dried, the treated plants were infested with third instar larvae of Heliothis virescens. The tests were running under greenhouse conditions at 24° C and 60% relative humitidy. Assessments to evaluate the initial effect of the immediate acitivity of the active ingredient were carried out 4, 24 and 48 hours after the infestation of the plants with the pests. Assessments to evaluate the initial effect of the activity over a prolonged period of the active ingredient were carried out as follows: the coated test plants were infested with the test individuals 2 and 8 days respectively after the application of the active ingredient. Each test was checked after 4, 24 and 48 hours. Test compounds

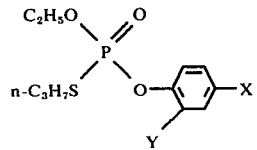

| | I | II | III |
| --- | --- | --- | --- |
| X | Br | Cl | Br |
| Y | Cl | Cl | Br |
| | Expl. 1 | Comp.26 US 3,839,511 | Comp.29 US 3,839,511 |
| toxicity mg/kg rat per Os | 400–900 | 400 | 300 |

| Time of Assessment in hours | % mortality | | | | | | | | |
| --- | --- | --- | --- | --- | --- | --- | --- | --- | --- |
| | compound I | | | compound II | | | compound III | | |
| | initial | residual | | initial | residual | | initial | residual | |
| | | 2d | 8d | | 2d | 8d | | 2d | 8d |
| 4 | 100 | 100 | 50 | 80 | 50 | 30 | 75 | 30 | 0 |
| 24 | 100 | 100 | 100 | 90 | 100 | 50 | 100 | 100 | 5 |
| 48 | 100 | 100 | 100 | 100 | 100 | 100 | 100 | 100 | 55 |

EXAMPLE 3

*Phaseolus vulgaris* (dwarf beans) had an infested piece of leaf from a mass culture of Tetranychus urticae placed on them 12 hours before the test for the acaricidal action. The occupying mobile stages were sprayed with the emulsified testing preparation from a chromatography atomiser so that the sprayed layer did not run off. The number of living and dead larvae, adults and eggs were evaluated after 7 days under a stereoscopic microscope and the result expressed in percentages. During the "interim", the treated plants were kept in greenhouse compartments at 25° C. The evaluation of the test proved good activity of the active ingredient.

EXAMPLE 4

A dust on a base of talcum and containing 5% active ingredient was applied to filter paper in concentrations of 100, 50, 25, 12.5 6.2 and 3.1 mg of active substance per m². Onto each of the treated substrates were applied 5 Necrobia rufipes, Rhyzoperta dominica, Anthrenus vorax and Tribolium confusum individuals respectively. Evaluation took place 24 hours later. Test compounds were same as set forth in Example 2.

| Test Animal | Dosage needed (mg a.i./m²) which provides a 100% control within 24 hours | | |
|---|---|---|---|
| | compound I | compound II | compound III |
| Necrobia rufipes | 3.1 | 6.2 | 6.2 |
| Tribolium confusum | 50 | 100 | >100 |
| Rhyzoperta dominica | 25 | 50 | 100 |
| Anthrenus vorax | 25 | 50 | 100 |

What we claim is:
1. A pesticidal composition which comprises as active ingredient the compound of the formula

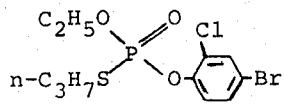

and a carrier.
2. The compound of the formula

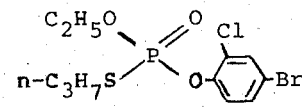

3. A method of controlling harmful insects and representatives of the order acarina which comprises applying thereto a pesticidally effective amount of the compound of the formula

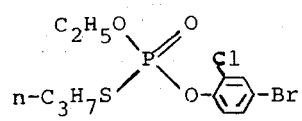

4. A method according to claim 3 which comprises controlling insects harmful to cotton and vegetables.

* * * * *